(12) United States Patent
Hempstead et al.

(10) Patent No.: US 9,707,031 B2
(45) Date of Patent: Jul. 18, 2017

(54) SURGICAL FORCEPS AND METHOD OF MANUFACTURING THEREOF

(71) Applicant: COVIDIEN LP, Mansfield, MA (US)

(72) Inventors: Russell D. Hempstead, Layfayette, CO (US); Keir Hart, Layfayette, CO (US)

(73) Assignee: COVIDIEN LP, Mansfield, MA (US)

( * ) Notice: Subject to any disclaimer, the term of this patent is extended or adjusted under 35 U.S.C. 154(b) by 9 days.

(21) Appl. No.: 14/717,636

(22) Filed: May 20, 2015

(65) Prior Publication Data

US 2015/0250529 A1 Sep. 10, 2015

Related U.S. Application Data

(63) Continuation of application No. 14/284,618, filed on May 22, 2014, now abandoned, which is a (Continued)

(51) Int. Cl.
| | |
|---|---|
| *A61B 18/14* | (2006.01) |
| *B29C 45/00* | (2006.01) |
| *A61B 18/00* | (2006.01) |
| *A61B 17/00* | (2006.01) |
| *B29L 31/00* | (2006.01) |

(52) U.S. Cl.
CPC ...... *A61B 18/1445* (2013.01); *A61B 18/1442* (2013.01); *B29C 45/0053* (2013.01); *A61B 2017/00526* (2013.01); *A61B 2018/0063* (2013.01); *A61B 2018/00077* (2013.01); *A61B 2018/00148* (2013.01); *B29C 2045/0079* (2013.01); *B29L 2031/7546* (2013.01); *Y10T 29/49117* (2015.01); *Y10T 29/49126* (2015.01); *Y10T 29/49155* (2015.01);
(Continued)

(58) Field of Classification Search
CPC ............ A61B 18/1445; A61B 18/1442; A61B 2018/00077; A61B 2018/0063; A61B 2018/00148; B29C 45/0053; B29C 2045/0079; Y10T 29/49155; Y10T 29/49162; Y10T 29/49126; Y10T 29/49158; Y10T 29/49117; Y10T 29/49885; B29L 2031/7546
See application file for complete search history.

(56) References Cited

U.S. PATENT DOCUMENTS

| | | |
|---|---|---|
| D249,549 S | 9/1978 | Pike |
| D263,020 S | 2/1982 | Rau, III |
| (Continued) | | |

FOREIGN PATENT DOCUMENTS

| | | |
|---|---|---|
| CN | 201299462 | 9/2009 |
| DE | 2415263 A1 | 10/1975 |
| (Continued) | | |

OTHER PUBLICATIONS

Int'l Search Report EP 04027479.7 dated Mar. 8, 2005.
(Continued)

*Primary Examiner* — John C Hong

(57) ABSTRACT

A method of manufacturing a forceps includes providing first and second jaw members and depositing an electrically-conductive tissue sealing plate atop each jaw member via vapor deposition. The jaw members are then coupled to one another to permit movement of one (or both) of the jaw members relative to the other between a spaced-apart position and an approximated position for grasping tissue between the tissue sealing plates thereof.

15 Claims, 7 Drawing Sheets

Related U.S. Application Data continuation of application No. 13/179,919, filed on Jul. 11, 2011, now Pat. No. 8,745,840.

(52) U.S. Cl.
CPC .... *Y10T 29/49158* (2015.01); *Y10T 29/49162* (2015.01); *Y10T 29/49885* (2015.01)

(56) References Cited

U.S. PATENT DOCUMENTS

| | | |
|---|---|---|
| D295,893 S | 5/1988 | Sharkany et al. |
| D295,894 S | 5/1988 | Sharkany et al. |
| D298,353 S | 11/1988 | Manno |
| D299,413 S | 1/1989 | DeCarolis |
| D343,453 S | 1/1994 | Noda |
| 5,277,201 A | 1/1994 | Stern |
| D348,930 S | 7/1994 | Olson |
| D349,341 S | 8/1994 | Lichtman et al. |
| D354,564 S | 1/1995 | Medema |
| D358,887 S | 5/1995 | Feinberg |
| 5,562,720 A | 10/1996 | Stern et al. |
| 5,573,534 A | 11/1996 | Stone |
| D384,413 S | 9/1997 | Zlock et al. |
| H1745 H | 8/1998 | Paraschac |
| D402,028 S | 12/1998 | Grimm et al. |
| D408,018 S | 4/1999 | McNaughton |
| D416,089 S | 11/1999 | Barton et al. |
| D424,694 S | 5/2000 | Tetzlaff et al. |
| D425,201 S | 5/2000 | Tetzlaff et al. |
| H1904 H | 10/2000 | Yates et al. |
| D449,886 S | 10/2001 | Tetzlaff et al. |
| D453,923 S | 2/2002 | Olson |
| D454,951 S | 3/2002 | Bon |
| D457,958 S | 5/2002 | Dycus et al. |
| D457,959 S | 5/2002 | Tetzlaff et al. |
| H2307 | 7/2002 | Yates et al. |
| D465,281 S | 11/2002 | Lang |
| D466,209 S | 11/2002 | Bon |
| D493,888 S | 8/2004 | Reschke |
| D496,997 S | 10/2004 | Dycus et al. |
| D499,181 S | 11/2004 | Dycus et al. |
| D502,994 S | 3/2005 | Blake, III |
| D509,297 S | 9/2005 | Wells |
| D525,361 S | 7/2006 | Hushka |
| 7,083,619 B2 | 8/2006 | Truckai et al. |
| 7,090,673 B2 | 8/2006 | Dycus et al. |
| D531,311 S | 10/2006 | Guerra et al. |
| 7,115,123 B2 | 10/2006 | Knowlton et al. |
| D533,274 S | 12/2006 | Visconti et al. |
| D533,942 S | 12/2006 | Kerr et al. |
| D535,027 S | 1/2007 | James et al. |
| D538,932 S | 3/2007 | Malik |
| D541,418 S | 4/2007 | Schechter et al. |
| D541,611 S | 5/2007 | Aglassinger |
| D541,938 S | 5/2007 | Kerr et al |
| D545,432 S | 6/2007 | Watanabe |
| D547,154 S | 7/2007 | Lee |
| D564,662 S | 3/2008 | Moses et al. |
| D567,943 S | 4/2008 | Moses et al. |
| D575,395 S | 8/2008 | Hushka |
| D575,401 S | 8/2008 | Hixson et al. |
| D582,038 S | 12/2008 | Swoyer et al. |
| D617,900 S | 6/2010 | Kingsley et al. |
| D617,901 S | 6/2010 | Unger et al. |
| D617,902 S | 6/2010 | Twomey et al. |
| D617,903 S | 6/2010 | Unger et al. |
| D618,798 S | 6/2010 | Olson et al. |
| D621,503 S | 8/2010 | Otten et al. |
| D627,462 S | 11/2010 | Kingsley |
| D628,289 S | 11/2010 | Romero |
| D628,290 S | 11/2010 | Romero |
| 7,828,798 B2 | 11/2010 | Buysse et al. |
| D630,324 S | 1/2011 | Reschke |
| 7,896,878 B2 | 3/2011 | Johnson et al. |
| 8,115,599 B2 | 2/2012 | Harazin et al. |
| 8,147,489 B2 | 4/2012 | Moses et al. |
| 8,298,233 B2 | 10/2012 | Mueller |
| 8,394,096 B2 | 3/2013 | Moses et al. |
| 8,409,246 B2 | 4/2013 | Kerr et al. |
| 8,409,247 B2 | 4/2013 | Garrison et al. |
| 8,425,511 B2 | 4/2013 | Olson |
| 8,430,877 B2 | 4/2013 | Kerr et al. |
| 8,439,913 B2 | 5/2013 | Horner et al. |
| 8,469,716 B2 | 6/2013 | Fedotov et al. |
| 8,469,991 B2 | 6/2013 | Kerr |
| 8,469,992 B2 | 6/2013 | Roy et al. |
| 8,480,671 B2 | 7/2013 | Mueller |
| 8,491,624 B2 | 7/2013 | Kerr et al. |
| 8,491,625 B2 | 7/2013 | Horner |
| 8,491,626 B2 | 7/2013 | Roy et al. |
| 8,512,336 B2 | 8/2013 | Couture |
| 8,540,749 B2 | 9/2013 | Garrison et al. |
| 8,551,091 B2 | 10/2013 | Couture et al. |
| 8,556,929 B2 | 10/2013 | Harper et al. |
| 8,568,397 B2 | 10/2013 | Horner et al. |
| 8,568,408 B2 | 10/2013 | Townsend et al. |
| 8,585,736 B2 | 11/2013 | Horner et al. |
| 8,597,295 B2 | 12/2013 | Kerr |
| 8,600,932 B2 | 12/2013 | Poling et al. |
| 8,623,018 B2 | 1/2014 | Horner et al. |
| 8,628,557 B2 | 1/2014 | Collings et al. |
| 8,641,712 B2 | 2/2014 | Couture |
| 8,647,343 B2 | 2/2014 | Chojin et al. |
| 8,652,135 B2 | 2/2014 | Nau, Jr. |
| 8,663,222 B2 | 3/2014 | Anderson et al. |
| 8,672,939 B2 | 3/2014 | Garrison |
| 8,685,009 B2 | 4/2014 | Chernov et al. |
| 8,685,021 B2 | 4/2014 | Chernov et al. |
| 8,702,749 B2 | 4/2014 | Twomey |
| 8,734,445 B2 | 5/2014 | Johnson et al. |
| 8,740,898 B2 | 6/2014 | Chojin et al. |
| 8,745,840 B2 | 6/2014 | Hempstead et al. |
| 8,784,418 B2 | 7/2014 | Romero |
| 8,795,269 B2 | 8/2014 | Garrison |
| 8,808,288 B2 | 8/2014 | Reschke |
| 8,814,864 B2 | 8/2014 | Gilbert |
| 2011/0082494 A1 | 4/2011 | Kerr et al. |
| 2011/0190765 A1 | 8/2011 | Chojin |
| 2011/0193608 A1 | 8/2011 | Krapohl |
| 2011/0251605 A1 | 10/2011 | Hoarau et al. |
| 2011/0270245 A1 | 11/2011 | Horner et al. |
| 2011/0270251 A1 | 11/2011 | Horner et al. |
| 2011/0276048 A1 | 11/2011 | Kerr et al. |
| 2011/0276049 A1 | 11/2011 | Gerhardt |
| 2011/0295313 A1 | 12/2011 | Kerr |
| 2011/0319888 A1 | 12/2011 | Mueller et al. |
| 2012/0041438 A1 | 2/2012 | Nau, Jr. et al. |
| 2012/0059372 A1 | 3/2012 | Johnson |
| 2012/0059375 A1 | 3/2012 | Couture et al. |
| 2012/0059408 A1 | 3/2012 | Mueller |
| 2012/0059409 A1 | 3/2012 | Reschke et al. |
| 2012/0083785 A1 | 4/2012 | Roy et al. |
| 2012/0083786 A1 | 4/2012 | Artale et al. |
| 2012/0083827 A1 | 4/2012 | Artale et al. |
| 2012/0095460 A1 | 4/2012 | Rooks et al. |
| 2012/0109187 A1 | 5/2012 | Gerhardt, Jr. et al. |
| 2012/0123402 A1 | 5/2012 | Chernov et al. |
| 2012/0123404 A1 | 5/2012 | Craig |
| 2012/0123410 A1 | 5/2012 | Craig |
| 2012/0130367 A1 | 5/2012 | Garrison |
| 2012/0136354 A1 | 5/2012 | Rupp |
| 2012/0172868 A1 | 7/2012 | Twomey et al. |
| 2012/0172924 A1 | 7/2012 | Allen, IV |
| 2012/0184989 A1 | 7/2012 | Twomey |
| 2012/0215219 A1 | 8/2012 | Roy et al. |
| 2012/0239034 A1 | 9/2012 | Horner et al. |
| 2012/0253344 A1 | 10/2012 | Dumbauld et al. |
| 2012/0259331 A1 | 10/2012 | Garrison |
| 2012/0265241 A1 | 10/2012 | Hart et al. |
| 2012/0283727 A1 | 11/2012 | Twomey |
| 2012/0296205 A1 | 11/2012 | Chernov et al. |
| 2012/0296238 A1 | 11/2012 | Chernov et al. |
| 2012/0296239 A1 | 11/2012 | Chernov et al. |
| 2012/0296323 A1 | 11/2012 | Chernov et al. |

(56) References Cited

U.S. PATENT DOCUMENTS

| | | |
|---|---|---|
| 2012/0296324 A1 | 11/2012 | Chernov et al. |
| 2012/0296333 A1 | 11/2012 | Twomey |
| 2012/0296334 A1 | 11/2012 | Kharin |
| 2012/0303025 A1 | 11/2012 | Garrison |
| 2012/0323238 A1 | 12/2012 | Tyrrell et al. |
| 2012/0330309 A1 | 12/2012 | Joseph |
| 2013/0018364 A1 | 1/2013 | Chernov et al. |
| 2013/0018371 A1 | 1/2013 | Twomey |
| 2013/0018372 A1 | 1/2013 | Sims et al. |
| 2013/0022495 A1 | 1/2013 | Allen, IV et al. |

FOREIGN PATENT DOCUMENTS

| | | |
|---|---|---|
| DE | 02514501 A1 | 10/1976 |
| DE | 2627679 A1 | 1/1977 |
| DE | 03423356 C2 | 6/1986 |
| DE | 03612646 A1 | 4/1987 |
| DE | 8712328 U1 | 2/1988 |
| DE | 04303882 C2 | 2/1995 |
| DE | 04403252 A1 | 8/1995 |
| DE | 19515914 C1 | 7/1996 |
| DE | 19506363 A1 | 8/1996 |
| DE | 29616210 U1 | 11/1996 |
| DE | 19608716 C1 | 4/1997 |
| DE | 19751106 A1 | 5/1998 |
| DE | 19751108 A1 | 5/1999 |
| DE | 10045375 C2 | 10/2002 |
| DE | 202007009165 U1 | 8/2007 |
| DE | 202007009317 U1 | 8/2007 |
| DE | 202007016233 U1 | 1/2008 |
| DE | 19738457 B4 | 1/2009 |
| DE | 102004026179 B4 | 1/2009 |
| DE | 102008018406 B3 | 7/2009 |
| EP | 1159926 A3 | 3/2003 |
| JP | 61-501068 | 9/1984 |
| JP | 10-24051 A | 1/1989 |
| JP | 11-47150 A | 6/1989 |
| JP | 6-502328 | 3/1992 |
| JP | 5-5106 | 1/1993 |
| JP | 05-40112 | 2/1993 |
| JP | 6-121797 A | 5/1994 |
| JP | 6-285078 A | 10/1994 |
| JP | 6-511401 | 12/1994 |
| JP | 06343644 A | 12/1994 |
| JP | 07265328 A | 10/1995 |
| JP | 8-56955 | 5/1996 |
| JP | 08252263 A | 10/1996 |
| JP | 8-317934 A | 12/1996 |
| JP | 9-10223 C | 1/1997 |
| JP | 9-122138 A | 5/1997 |
| JP | 10-155798 A | 6/1998 |
| JP | 11-070124 A | 3/1999 |
| JP | 11-169381 A | 6/1999 |
| JP | 11-192238 A | 7/1999 |
| JP | 11244298 A | 9/1999 |
| JP | 2000-102545 A | 4/2000 |
| JP | 2000342599 A | 12/2000 |
| JP | 2000350732 A | 12/2000 |
| JP | 2001-8944 | 1/2001 |
| JP | 2001-29356 | 2/2001 |
| JP | 2001128990 A | 5/2001 |
| JP | 2001-190564 A | 7/2001 |
| JP | 2004-517668 A | 6/2004 |
| JP | 2004-528869 A | 9/2004 |
| SU | 401367 A1 | 10/1973 |
| WO | 0036986 A1 | 6/2000 |
| WO | 0115614 A1 | 3/2001 |
| WO | 0154604 A1 | 8/2001 |
| WO | 2005/110264 A2 | 11/2005 |

OTHER PUBLICATIONS

Int'l Search Report EP 04709033.7 dated Dec. 8, 2010.
Int'l Search Report EP 04752343.6 dated Jul. 20, 2007.
Int'l Search Report EP 05002671.5 dated Dec. 22, 2008.
Int'l Search Report EP 05019130.3 dated Oct. 27, 2005.
Int'l Search Report EP 05017281.6 dated Nov. 24, 2005.
Int'l Search Report EP 05019429.9 dated May 6, 2008.
Int'l Search Report EP 09 168153.6 dated Jan. 14, 2010.
Int'l Search Report—extended—EP 05021937.7 dated Mar. 15, 2006.
Int'l Search Report EP 05023017.6 dated Feb. 24, 2006.
Int'l Search Report EP 06002279.5 dated Mar. 30, 2006.
Int'l Search Report EP 06005185.1 dated May 10, 2006.
Int'l Search Report EP 06006716.2 dated Aug. 4, 2006.
Int'l Search Report EP 06008779.8 dated Jul. 13, 2006.
Int'l Search Report EP 98944778.4 dated Oct. 31, 2000.
Int'l Search Report EP 06024123.9 dated Mar. 6, 2007.
Int'l Search Report EP 07 013779.9 dated Oct. 26, 2007.
Int'l Search Report Extended—EP 07 009029.5 dated Jul. 20, 2007.
Int'l Search Report EP 07 016911 dated May 28, 2010.
Int'l Search Report EP 07 021646.0 dated Mar. 20, 2008.
Int'l Search Report EP 07 021647.8 dated May 2, 2008.
Int'l Search Report EP 08 006917.2 dated Jul. 3, 2008.
Int'l Search Report EP 08 020807.7 dated Apr. 24, 2009.
Int'l Search Report EP 09 003677.3 dated May 4, 2009.
Int'l Search Report EP 09 172749.5 dated Dec. 4, 2009.
Int'l Search Report EP 11 006233.8 dated Feb. 2, 2012.
Int'l Search Report EP 10 175956.1 dated Nov. 12, 2010.
Int'l Search Report EP 10 185386.9 dated Jan. 10, 2011.
Int'l Search Report EP 10 160870,1 dated Aug. 9, 2010.
Int'l Search Report EP 10 181034.9 dated Jan. 26, 2011.
Int'l Search Report EP 10 181575.1 dated Apr. 5, 2011.
Int'l Search Report EP 10 181969.6 dated Feb. 4, 2011.
Int'l Search Report EP 10 186527.7 dated Jun. 17, 2011.
Int'l Search Report EP 11 151509.4 dated Jun. 6, 2011.
Int'l Search Report EP 11 152220.7 dated May 19, 2011.
Int'l Search Report EP 11 152360.1 dated Jun. 6, 2011.
Int'l Search Report EP 11 161117.4 dated Jun. 30, 2011.
Int'l Search Report PCT/US98/18640 dated Jan. 29, 1999.
Int'l Search Report PCT/US98/23950 dated Jan. 14, 1999.
Int'l Search Report PCT/US98/24281 dated Feb. 22, 1999.
Int'l Search Report PCT/US99/24869 dated Feb. 3, 2000.
Int'l Search Report PCT/US01/11218 dated Aug. 14, 2001.
Int'l Search Report PCT/US01/11224 dated Nov. 13, 2001.
Int'l Search Report PCT/US01/11340 dated Aug. 16, 2001.
Int'l Search Report PCT/US01/11420 dated Oct. 16, 2001.
Int'l Search Report PCT/US02/01890 dated Jul. 25, 2002.
Int'l Search Report PCT/US02/11100 dated Jul. 16, 2002.
Int'l Search Report PCT/US03/08146 dated Aug. 8, 2003.
Michael Choti, "Abdominoperineal Resection with the LigaSure Vessel Sealing System and LigaSure Atlas 20 cm Open Instrument" ; Innovations That Work, Jun. 2003.
Chung et al., "Clinical Experience of Sutureless Closed Hemorrhoidectomy with LigaSure" Diseases of the Colon & Rectum vol. 46, No. 1 Jan. 2003.
Tinkcler L.F., "Combined Diathermy and Suction Forceps" , Feb. 6, 1967 (Feb. 6, 1965), British Medical Journal Feb. 6, 1976, vol. 1, nr. 5431 p. 361, ISSN: 0007-1447.
Carbonell et al., "Comparison of theGyrus PlasmaKinetic Sealer and the Valleylab LigaSure Device in the Hemostasis of Small, Medium, and Large-Sized Arteries" Carolinas Laparoscopic and Advanced Surgery Program, Carolinas Medical Center,Charlotte,NC; Date: Aug. 2003.
Peterson et al. "Comparison of Healing Process Following Ligation with Sutures and Bipolar Vessel Sealing" Surgical Technology International (2001).
"Electrosurgery: A Historical Overview" Innovations in Electrosurgery; Sales/Product Literature; Dec. 31, 2000.
Johnson et al. "Evaluation of a Bipolar Electrothermal Vessel Sealing Device in Hemorrhoidectomy" Sales/Product Literature; Jan. 2004.
E. David Crawford "Evaluation of a New Vessel Sealing Device in Urologic Cancer Surgery", 2000.
Johnson et al. "Evaluation of the LigaSure Vessel Sealing System in Hemorrhoidectomy" American College of Surgeons (ACS) Clinicla Congress Poster (2000).

(56) References Cited

OTHER PUBLICATIONS

Muller et al., "Extended Left Hemicolectomy Using the LigaSure Vessel Sealing System" Innovations That Work, Sep. 1999.
Kennedy et al. "High-burst-strength, feedback-controlled bipolar vessel sealing" Surgical Endoscopy (1998) 12: 876-878.
Burdette et al. "In Vivo Probe Measurement Technique for Determining Dielectric Properties at VHF Through Microwave Frequencies", IEEE Transactions on Microwave Theory and Techniques, vol. MTT-28, No. 4, Apr. 1980 pp. 414-427.
Carus et al., "Initial Experience With The LigaSure Vessel Sealing System in Abdominal Surgery" Innovations That Work, Jun. 2002.
Heniford et al. "Initial Research and Clinical Results with an Electrothermal Bipolar Vessel Sealer" Oct. 1999.
Heniford et al. "Initial Results with an Electrothermal Bipolar Vessel Sealer" Surgical Endoscopy (2000) 15:799-801.
Herman et al., "Laparoscopic Intestinal Resection With the LigaSure Vessel Sealing System: A Case Report"; Innovations That Work, Feb. 2002.
Koyle et al., "Laparoscopic Palomo Varicocele Ligation in Children and Adolescents" Pediatric Endosurgery & Innovative Techniques, vol. 6, No. 1, 2002.
W. Scott Helton, "LigaSure Vessel Sealing System: Revolutionary Hemostasis Product for General Surgery"; Sales/Product Literature 1999.
LigaSure Vessel Sealing System, the Seal of Confidence in General, Gynecologic, Urologic, and Laparaoscopic Surgery; Sales/Product Literature; Apr. 2002.
Joseph Ortenberg "LigaSure System Used in Laparoscopic 1st and 2nd Stage Orchiopexy" Innovations That Work, Nov. 2002.
Sigel et al. "The Mechanism of Blood Vessel Closure by High Frequency Electrocoagulation" Surgery Gynecology & Obstetrics, Oct. 1965 pp. 823-831.
Sampayan et al, "Multilayer Ultra-High Gradient Insulator Technology" Discharges and Electrical Insulation in Vacuum, 1998. Netherlands Aug. 17-21, 1998; vol. 2, pp. 740-743.
Paul G. Horgan, "A Novel Technique for Parenchymal Division During Hepatectomy" The American Journal of Surgery, vol. 181, No. 3, Apr. 2001 pp. 236-237.
Benaron et al., "Optical Time-of-Flight and Absorbance Imaging of Biologic Media", Science, American Association for the Advancement of Science, Washington, DC, vol. 259, Mar. 5, 1993, pp. 1463-1466.
Olsson et al. "Radical Cystectomy in Females" Current Surgical Techniques in Urology, vol. 14, Issue 3, 2001.
Palazzo et al. "Randomized clinical trial of Ligasure versus open haemorrhoidectomy" British Journal of Surgery 2002, 89, 154-157.
Levy et al. "Randomized Trial of Suture Versus Electrosurgical Bipolar Vessel Sealing in Vaginal Hysterectomy" Obstetrics & Gynecology, vol. 102, No. 1, Jul. 2003.
"Reducing Needlestick Injuries in the Operating Room", 2001.
Bergdahl et al. "Studies on Coagulation and the Development of an Automatic Computerized Bipolar Coagulator" J. Neurosurg, vol. 75, Jul. 1991, pp. 148-151.
Strasberg et al. "A Phase I Study of the LigaSure Vessel Sealing System in Hepatic Surgery" Section of HPB Surger, Washington University School of Medicine, St. Louis MO, Presented at AHPBA, Feb. 2001.
Sayfan et al. "Sutureless Closed Hemorrhoidectomy: A New Technique" Annals of Surgery vol. 234 No. 1 Jul. 2001; pp. 21-24.
Levy et al., "Update on Hysterectomy—New Technologies and Techniques," OBG Management, Feb. 2003.
Dulemba et al. "Use of a Bipolar Electrothermal Vessel Sealer in Laparoscopically Assisted Vaginal Hysterectomy" Sales/Product Literature; Jan. 2004.
Strasberg et al., "Use of a Bipolar Vessel-Sealing Device for Parenchymal Transection During Liver Surgery" Journal of Gastrointestinal Surgery, vol. 6, No. 4, Jul./Aug. 2002 pp. 569-574.
Sengupta et al., "Use of a Computer-Controlled Bipolar Diathermy System in Radical Prostatectomies and Other Open Urological Surgery" ANZ Journal of Surgery (2001) 71.9 pp. 538-540.
Rothenberg et al. "Use of the LigaSure Vessel Sealing System in Minimally Invasive Surgery in Children" Int'l Pediatric Endosurgery Group (IPEG) 2000.
Crawford et al. "Use of the LigaSure Vessel Sealing System in Urologic Cancer Surgery" Grand Rounds in Urology 1999 vol. 1 Issue 4 pp. 10-17.
Craig Johnson, "Use of the LigaSure Vessel Sealing System in Bloodless Hemorrhoidectomy" Innovations That Work, Mar. 2000.
Levy et al. "Use of a New Energy-based Vessel Ligation Device During Vaginal Hysterectomy" Int'l Federation of Gynecology and Obstetrics (FIGO) World Congress 1999.
Barbara Levy, "Use of a New Vessel Ligation Device During Vaginal Hysterectomy" FIGO 2000, Washington, D.C..
E. David Crawford "Use of a Novel Vessel Sealing Technology in Management of the Dorsal Veinous Complex", 2000.
Jarrett et al., "Use of the LigaSure Vessel Sealing System for Peri-Hilar Vessels in Laparoscopic Nephrectomy" Sales/Product Literature 2000.
Crouch et al. "A Velocity-Dependent Model for Needle Insertion in Soft Tissue" MICCAI 2005; LNCS 3750 pp. 624-632, Dated: 2005.
McLellan et al. "Vessel Sealing for Hemostasis During Pelvic Surgery" Int'l Federation of Gynecology and Obstetrics FIGO World Congress 2000, Washington, D.C..
McLellan et al. "Vessel Sealing for Hemostasis During Gynecologic Surgery" Sales/Product Literature 1999.
Int'l Search Report EP 98957771 dated Aug. 9, 2001.
Int'l Search Report EP 98957773 dated Aug. 1, 2001.
Int'l Search Report EP 98958575.7 dated Sep. 20, 2002.
Int'l Search Report EP 04013772.1 dated Apr. 1, 2005.
Int'l Search Report PCT/US03/18674 dated Sep. 18, 2003.
Int'l Search Report PCT/US03/18676 dated Sep. 19, 2003.
Int'l Search Report PCT/US03/28534 dated Dec. 19, 2003.
Int'l Search Report PCT/US04/03436 dated Mar. 3, 2005.
Int'l Search Report PCT/US04/13273 dated Dec. 15, 2004.
Int'l Search Report PCT/US04/15311 dated Jan. 12, 2005.
Int'l Search Report PCT/US07/021438 dated Apr. 1, 2008.
Int'l Search Report PCT/US07/021440 dated Apr. 8, 2008.
Int'l Search Report PCT/US08/52460 dated Apr. 24, 2008.
Int'l Search Report PCT/US08/61498 dated Sep. 22, 2008.
Int'l Search Report PCT/US09/032690 dated Jun. 16, 2009.

SURGICAL FORCEPS AND METHOD OF MANUFACTURING THEREOF

CROSS-REFERENCE TO RELATED APPLICATION

The present application is a continuation application of and claims the priority to U.S. patent application Ser. No. 14/284,618, filed on May 22, 2014, which is a continuation of U.S. patent application Ser. No. 13/179,919, filed on Jul. 11, 2011, now U.S. Pat. No. 8,745,840, the entire contents of each of these applications is incorporated herein by reference.

BACKGROUND

Technical Field

The present disclosure relates to surgical instruments and, more particularly, to surgical forceps and methods of manufacturing surgical forceps.

Background of Related Art

A forceps is a plier-like instrument which relies on mechanical action between its jaws to grasp, clamp and constrict vessels or tissue. Electrosurgical forceps utilize both mechanical clamping action and electrical energy to affect hemostasis by heating tissue and blood vessels to coagulate and/or cauterize tissue. Certain surgical procedures require more than simply cauterizing tissue and rely on the unique combination of clamping pressure, precise electrosurgical energy control and gap distance (i.e., distance between opposing jaw members when closed about tissue) to "seal" tissue, vessels and certain vascular bundles. Typically, once a vessel is sealed, the surgeon has to accurately sever the vessel along the newly formed tissue seal. Accordingly, many vessel sealing instruments have been designed which incorporate a knife or blade member that effectively severs the tissue after forming a tissue seal.

SUMMARY

In accordance with one embodiment of the present disclosure, a method of manufacturing a forceps is provided. The method includes providing first and second jaw members and depositing an electrically-conductive tissue sealing plate atop each jaw member via vapor deposition. The jaw members are then coupled to one another to permit movement of one (or both) of the jaw members between a spaced-apart position and an approximated position for grasping tissue between the tissue sealing plates thereof.

In one embodiment, the vapor deposited includes physical vapor deposition. Alternatively, the vapor deposition may include chemical vapor deposition.

In another embodiment, the tissue sealing plates are deposited atop insulators of the jaw members. The insulators may be formed via injection molding and/or may be engaged within jaw frames of the respective jaw members, e.g., via snap-fitting.

In yet another embodiment, each of the jaw frames includes a proximal flange extending proximally therefrom. The proximal flanges may be pivotably coupled to one another to permit movement of the jaw members relative to one another between the spaced-apart position and the approximated position.

In still another embodiment, the method further includes molding a wire within one (or both) of the jaw members such that the wire is disposed in electrically communication with the tissue sealing plate thereof for supplying electrosurgical energy to the tissue sealing plate.

A method of manufacturing a jaw member of a forceps is provided in accordance with another embodiment of the present disclosure. The method includes providing an insulator and a jaw frame, forming an electrically-conductive tissue sealing plate atop the insulator via vapor deposition, and engaging the insulator to the jaw frame.

In one embodiment, the insulator is formed via injection molding. The vapor deposition may include physical vapor deposition, chemical vapor deposition, or other suitable deposition process.

In yet another embodiment, a wire is molded to the insulator prior to forming the tissue sealing plate atop the insulator. When the tissue sealing plate is formed atop the insulator, the tissue sealing plate is disposed in electrical communication with the wire.

Another method of manufacturing a jaw member of a forceps is provided in accordance with the present disclosure. In this embodiment, the method includes injection molding an insulator and vapor depositing an electrically-conductive tissue sealing plate atop the insulator.

The method may further include engaging the insulator to a jaw frame and/or electrically coupling the tissue sealing plate to a source of electrosurgical energy, e.g., via a wire molded to the insulator and disposed in electrical communication with the tissue sealing plate.

BRIEF DESCRIPTION OF THE DRAWINGS

Various embodiments of the present disclosure are described herein with reference to the drawings wherein.

DETAILED DESCRIPTION

Figure 1:
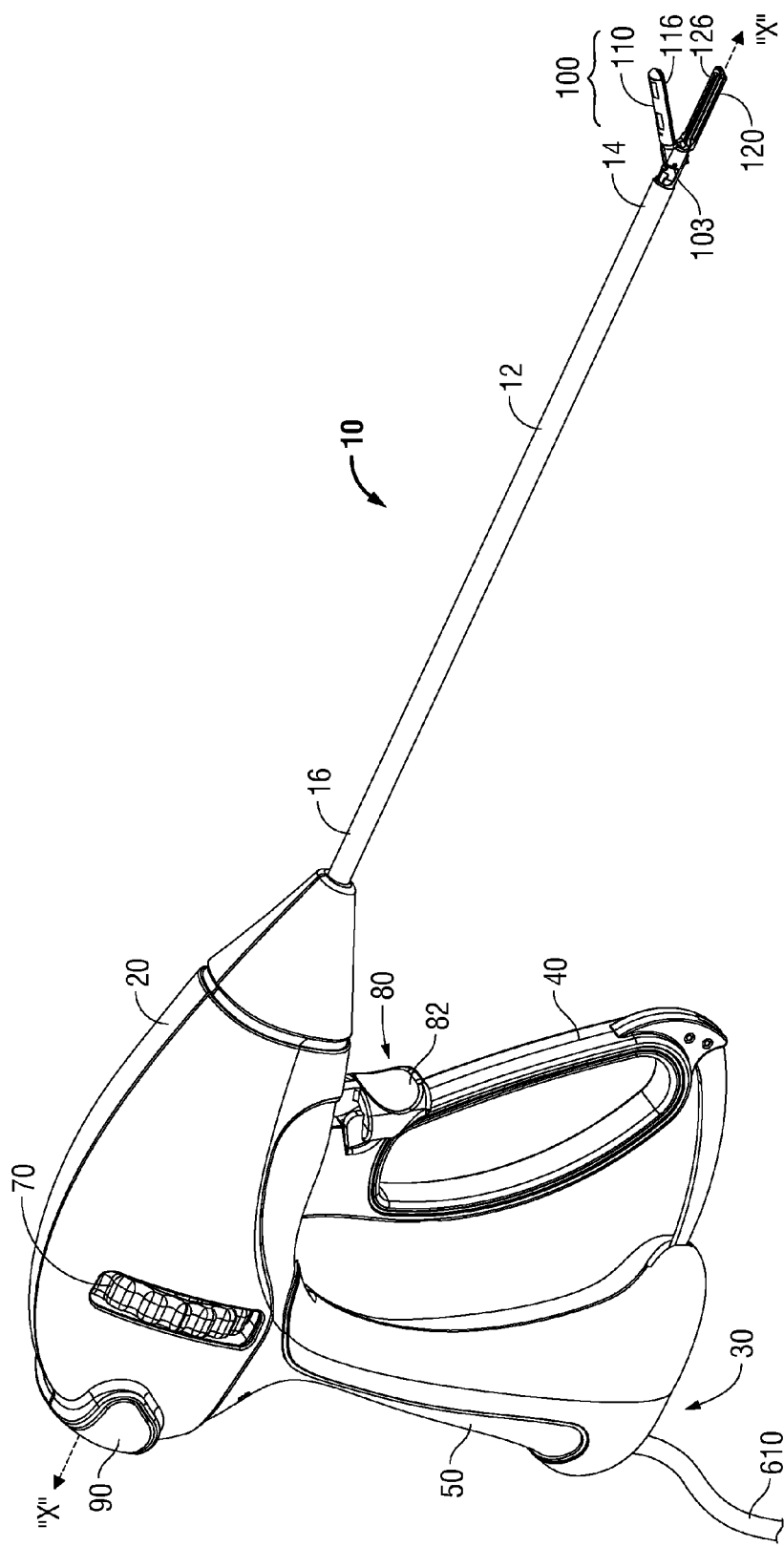
FIG. 1 is a front, perspective view of an endoscopic surgical forceps configured for use in accordance with the present disclosure.

Embodiments of the present disclosure are described in detail with reference to the drawing figures wherein like reference numerals identify similar or identical elements. As used herein, the term "distal" refers to the portion that is being described which is further from a user, while the term "proximal" refers to the portion that is being described which is closer to a user.

Figure 2:
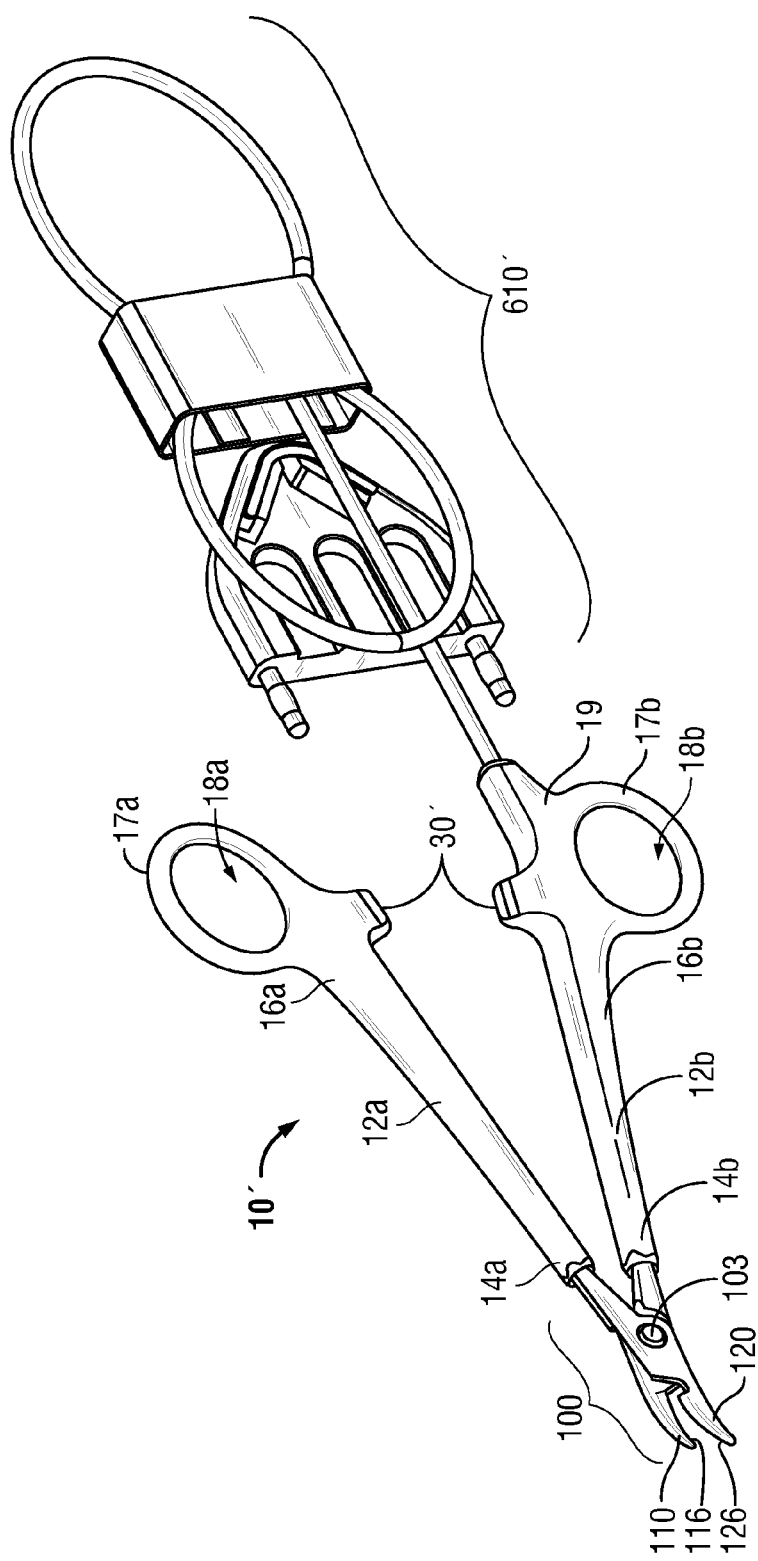
FIG. 2 is a front, perspective view of an open surgical forceps configured for use in accordance with the present disclosure.

Referring now to FIGS. 1 and 2, FIG. 1 depicts a forceps 10 for use in connection with endoscopic surgical procedures and FIG. 2 depicts an open forceps 10' contemplated for use in connection with traditional open surgical procedures. For the purposes herein, either an endoscopic instrument, e.g., forceps 10, or an open instrument, e.g., forceps 10', may be utilized in accordance with the present disclosure. Obviously, different electrical and mechanical connections and considerations apply to each particular type of instrument; however, the novel aspects with respect to the end effector assembly and its operating characteristics remain generally consistent with respect to both the open and endoscopic configurations.

Turning now to FIG. 1, an endoscopic forceps 10 is provided defining a longitudinal axis "X-X" and including a housing 20, a handle assembly 30, a rotating assembly 70, a trigger assembly 80 and an end effector assembly 100. Forceps 10 further includes a shaft 12 having a distal end 14 configured to mechanically engage end effector assembly 100 and a proximal end 16 that mechanically engages housing 20. Forceps 10 also includes electrosurgical cable 610 that connects forceps 10 to a generator (not shown) or other suitable power source, although forceps 10 may alternatively be configured as a battery powered instrument. Cable 610 includes a wire (or wires) (not shown) extending therethrough that has sufficient length to extend through shaft 12 in order to provide electrical energy to at least one of the sealing plates 116, 126 of jaw members 110, 120, respectively, of end effector assembly 100, e.g., upon activation of activation switch 90.

With continued reference to FIG. 1, handle assembly 30 includes fixed handle 50 and a moveable handle 40. Fixed handle 50 is integrally associated with housing 20 and handle 40 is moveable relative to fixed handle 50. Rotating assembly 70 is rotatable in either direction about longitudinal axis "X-X" to rotate end effector 100 about longitudinal axis "X-X." Housing 20 houses the internal working components of forceps 10.

End effector assembly 100 is shown attached at a distal end 14 of shaft 12 and includes a pair of opposing jaw members 110 and 120. Each of the jaw members 110 and 120 includes an opposed electrically conductive tissue-sealing plate 116, 126, respectively. End effector assembly 100 is designed as a unilateral assembly, i.e., where jaw member 120 is fixed relative to shaft 12 and jaw member 110 is moveable about pivot 103 relative to shaft 12 and fixed jaw member 120. However, end effector assembly 100 may alternatively be configured as a bilateral assembly, i.e., where both jaw member 110 and jaw member 120 are moveable about a pivot 103 relative to one another and to shaft 12. In some embodiments, a knife assembly (not shown) is disposed within shaft 12 and a knife channel 125 (FIG. 3) is defined within one or both jaw members 110, 120 to permit reciprocation of a knife blade (not shown) therethrough, e.g., via activation of a trigger 82 of trigger assembly 80. The particular features of end effector assembly 100 will be described in greater detail hereinbelow.

Continuing with reference to FIG. 1, moveable handle 40 of handle assembly 30 is ultimately connected to a drive assembly (not shown) that, together, mechanically cooperate to impart movement of jaw members 110 and 120 between a spaced-apart position and an approximated position to grasp tissue between sealing plates 116 and 126 of jaw members 110, 120, respectively. As shown in FIG. 1, moveable handle 40 is initially spaced-apart from fixed handle 50 and, correspondingly, jaw members 110, 120 are in the spaced-apart position. Moveable handle 40 is actuatable from this initial position to a depressed position corresponding to the approximated position of jaw members 110, 120.

Referring now to FIG. 2, an open forceps 10' is shown including two elongated shafts 12a and 12b, each having a proximal end 16a and 16b, and a distal end 14a and 14b, respectively. Similar to forceps 10 (FIG. 1), forceps 10' is configured for use with end effector assembly 100. More specifically, end effector assembly 100 is attached to distal ends 14a and 14b of shafts 12a and 12b, respectively. As mentioned above, end effector assembly 100 includes a pair of opposing jaw members 110 and 120 that is pivotably connected about a pivot 103. Each shaft 12a and 12b includes a handle 17a and 17b disposed at the proximal end 16a and 16b thereof. Each handle 17a and 17b defines a finger hole 18a and 18b therethrough for receiving a finger of the user. As can be appreciated, finger holes 18a and 18b facilitate movement of the shafts 12a and 12b relative to one another which, in turn, pivots jaw members 110 and 120 from an open position, wherein the jaw members 110 and 120 are disposed in spaced-apart relation relative to one another, to a closed position, wherein the jaw members 110 and 120 cooperate to grasp tissue therebetween.

A ratchet 30' may be included for selectively locking the jaw members 110 and 120 relative to one another at various positions during pivoting. Ratchet 30' may include graduations or other visual markings that enable the user to easily and quickly ascertain and control the amount of closure force desired between the jaw members 110 and 120.

With continued reference to FIG. 2, one of the shafts, e.g., shaft 12b, includes a proximal shaft connector 19 that is designed to connect the forceps 10' to a source of electrosurgical energy such as an electrosurgical generator (not shown). Proximal shaft connector 19 secures an electrosurgical cable 610' to forceps 10' such that the user may selectively apply electrosurgical energy to the electrically conductive sealing plates 116 and 126 of jaw members 110 and 120, respectively, as needed.

Forceps 10' may further include a knife assembly (not shown) disposed within either of shafts 12a, 12b and a knife channel 125 (FIG. 3) defined within one or both of jaw members 110, 120, respectively, to permit reciprocation of a knife blade (not shown) therethrough.

Figure 3:
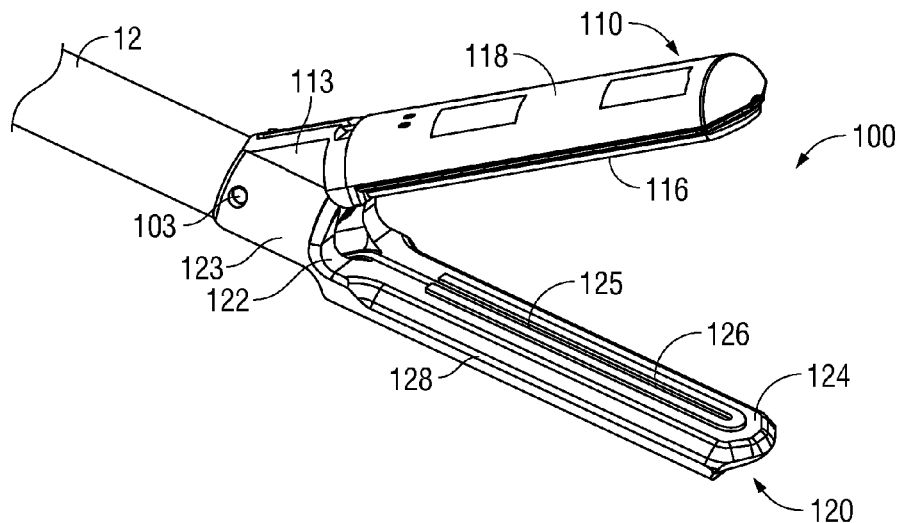
FIG. 3 is an enlarged, front, perspective view of an end effector assembly configured for use with the forceps of FIGS. 1 and 2.
Figure 4:
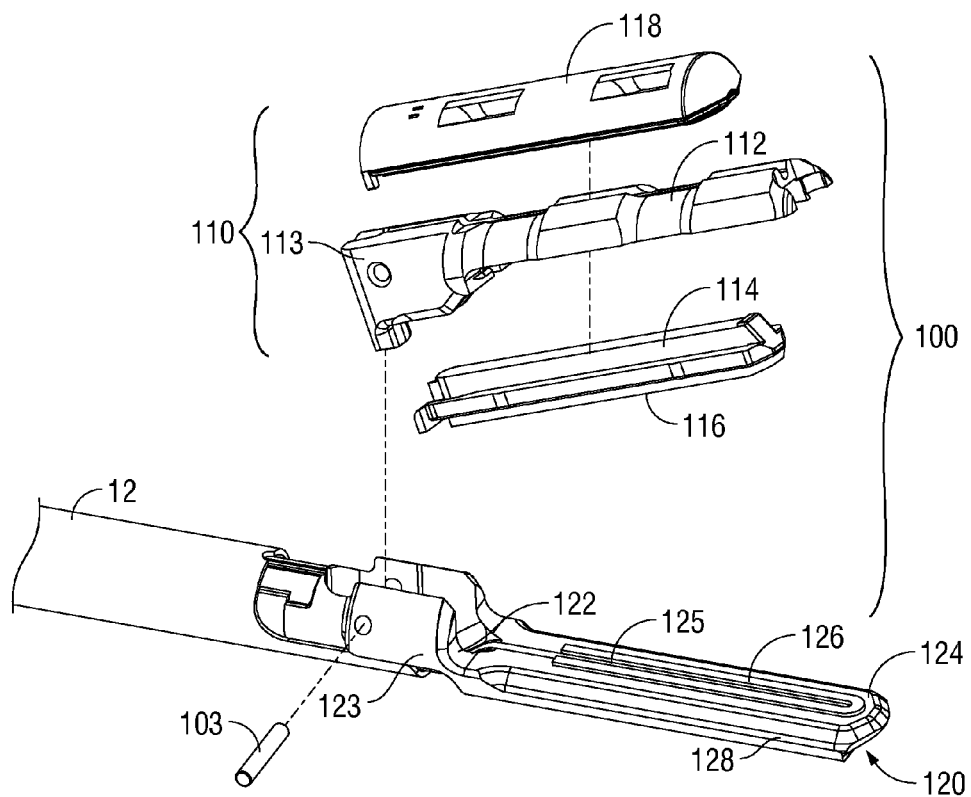
FIG. 4 is an enlarged, front, perspective view of the end effector assembly of FIG. 3 wherein one of the jaw members of the end effector assembly is shown with parts separated.

Turning now to FIGS. 3-4, end effector assembly 100, including jaw members 110 and 120 is configured for use with either forceps 10 or forceps 10', discussed above, or any other suitable surgical instrument capable of pivoting jaw members 110, 120 relative to one another between a spaced-apart position and an approximated position for grasping tissue therebetween. However, for purposes of simplicity and consistency, end effector assembly 100 will be described hereinbelow with reference to forceps 10 only. Further, jaw members 110, 120 are substantially similar to one another and, thus, the features described herein with respect to jaw member 110 or jaw member 120 apply similarly to the other jaw member 110, 120.

With continued reference to FIGS. 3-4, jaw members 110, 120 each include a jaw frame 112, 122, an insulator 114, 124 engaged to the respective jaw frame 112, 122 thereof, an electrically-conductive tissue sealing plate 116, 126 disposed atop insulator 114, 124, respectively, and an outer jaw housing 118, 128 configured to house the components of jaw members 110, 120, respectively, therein. Jaw frames 112, 122 each include a proximal flange 113, 123 extending proximally therefrom. Jaw frames 112, 122 and proximal flanges 113, 123 of each jaw member 110, 120, respectively, are formed as a single, monolithic component. Proximal flanges 113, 123 are pivotably coupled to one another via pivot pin 103 to permit pivotable movement of jaw members 110, 120 relative to one another between the spaced-apart position and the approximated position for grasping tissue therebetween. Jaw frames 112, 122 are further configured, as mentioned above, to engage insulators 114, 124, respectively, thereon. Insulators 114, 124, in turn, are configured to receive electrically-conductive tissue sealing plates 116, 126, respectively, thereon such that tissue sealing plates 116, 126 of jaw members 110, 120, respectively, oppose one another. Accordingly, when jaw members 110, 120 are moved to the approximated position with tissue disposed therebetween, tissue is grasped between the opposed tissue sealing plates 116, 126 of jaw members 110, 120, respectively. Further, one or both of tissue sealing plates 116, 126 is adapted to connect to a source of electrosurgical energy (not shown) for conducting energy therebetween and through tissue to seal tissue grasped between jaw members 110, 120. Various configurations of and methods for manufacturing end effector assembly 100, or the components thereof, are described in detail hereinbelow.

Figure 5A:
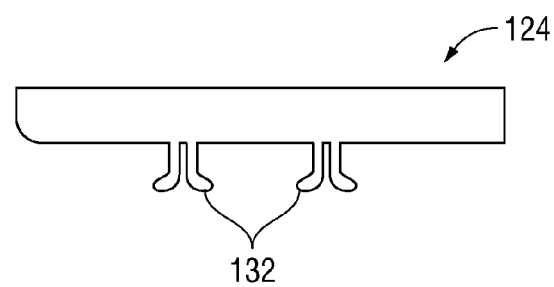
FIG. 5A is a longitudinal, cross-sectional view of one embodiment of an insulator configured for use with one of the jaw members of the end effector assembly of FIG. 3.
Figure 5B:
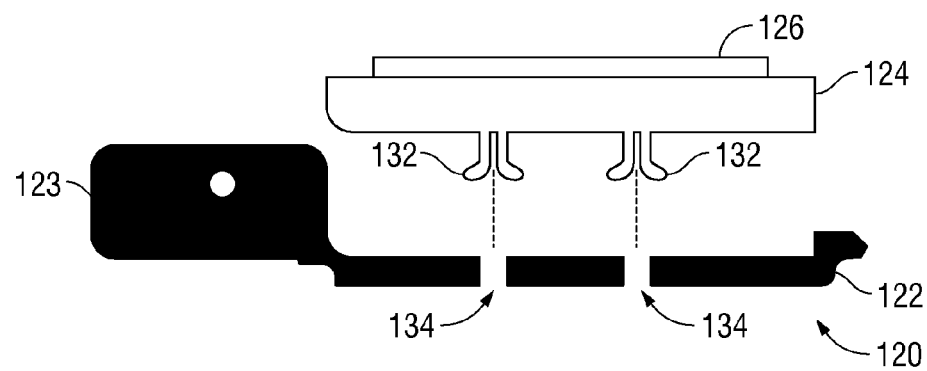
FIG. 5B is a longitudinal, cross-sectional view of the insulator of FIG. 5A including a sealing plate disposed thereon and in position for assembly with a jaw frame of the jaw member.
Figure 5C:
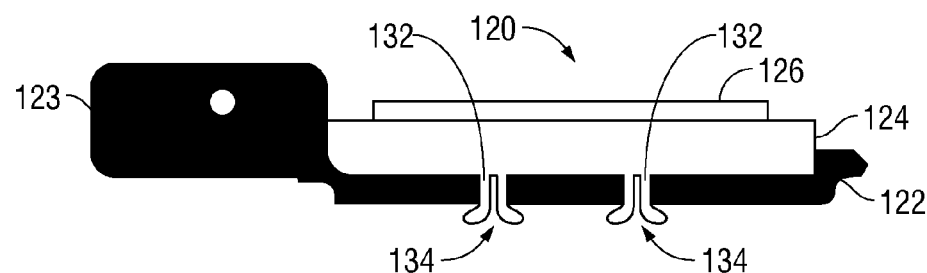
FIG. 5C is a longitudinal, cross-sectional view of the jaw member of FIG. 5B in an assembled condition.

Referring now to FIGS. 5A-5C, the configuration and manufacture of jaw member 120 in accordance with an embodiment of the present disclosure is described. The configuration and manufacture of jaw member 110 is similar to that of jaw member 120 and, thus, is not described to avoid unnecessary repetition. As mentioned above, jaw member 120 includes a jaw frame 122 including a proximal flange 123 extending proximally therefrom, an insulator 124, and a tissue sealing plate 126. Jaw frame 122, including proximal flange 123 is formed from stainless steel, or other suitable material that is sufficiently strong and rigid to permit accurate and consistent movement of jaw members 110, 120 between the spaced-apart and approximated positions for grasping tissue therebetween, to ensure that an accurate and consistent closure pressure is imparted to tissue grasped between jaw members 120, and to retain the other components of jaw member 120 in position thereon. Insulator 124 may formed from an electrically-insulative material and is configured to electrically insulate tissue sealing plate 126 from the remaining components of jaw member 120, e.g., jaw frame 122. Insulator 124 may be formed via injection-molding, or any other suitable manufacturing process. Tissue sealing plate 126 may be formed from any suitable electrically-conductive material and is disposed on insulator 124. Tissue sealing plate 126 is configured, in conjunction with tissue sealing plate 116 of jaw member 110 (FIGS. 3-4), to grasp and seal tissue disposed between jaw members 110, 120 (FIGS. 3-4).

Continuing with reference to FIGS. 5A-5C, and initially to FIG. 5A, during manufacturing, insulator 124 and tissue sealing plate 126 are formed as a single component, thus obviating the need to mechanically, or otherwise engage tissue sealing plate 126 to insulator 124 and/or other components of jaw member 120. Such a configuration also reduces part count, obviates the need to form more complex features into insulator 124 and tissue sealing plate 126 for engaging these components to one another, and/or obviates the need for more complex assembly processes. In particular, tissue sealing plate 126 may be formed atop insulator 124 during manufacturing via vapor deposition (vacuum deposition), e.g., physical vapor deposition or chemical vapor deposition. Physical vapor deposition involves heating a material, e.g., the material to form tissue sealing plate 126, to a vaporous state and exposing the vaporous material to a substrate, e.g., insulator 124, such that the vaporous material is deposited, or condensates on the surface of the substrate, thereby forming a film, or plate of material disposed on the substrate. Such a process may be used to deposit sufficient material onto insulator 124 so as to form tissue sealing plate 126 thereon.

Chemical vapor deposition involves exposing a substrate, e.g., insulator 124, to one or more precursors that react with one another and/or decompose to form a thin film, or plate of deposit on the surface of the substrate. As such, the precursors may be selected so as to produce the material to form tissue sealing plate 126, such that chemical vapor deposition may be used to form tissue sealing plate 126 on insulator 124. Other similar, suitable processes for depositing, or forming tissue sealing plate 126 on insulator 124 include thermal spraying, metallizing (vacuum metalizing), and other vacuum deposition processes.

With continued reference to FIGS. 5A-5C, and to FIG. 5B in particular, with tissue sealing plate 126 formed on insulator 124 as a single component, e.g., via vapor deposition, insulator 124 may be engaged to jaw frame 122 of jaw member 120. Insulator 124 includes a pair of snap-fit members 132 configured to snap-fittingly engage corresponding apertures 134 defined through jaw frame 122 to engage insulator 124 and, thus, tissue sealing plate 126, atop jaw frame 122. More specifically, in order to engage insulator 124 to jaw frame 122, snap-fit members 132 of insulator 124 are urged into apertures 134 of jaw frame 122, thereby resiliently compressing snap-fit members 132 to accommodate snap-fit members 132 within apertures 134. Upon further translation of snap-fit members 132 through apertures 134, snap-fit members 132 eventually extend from apertures 134 on the opposite side of jaw frame 122, thus allowing snap-fit members 132 to resiliently bias, or snap, back to the initial, uncompressed condition. With snap-fit members 132 disposed through apertures 134 in the uncompressed condition, snap-fit members 132 are inhibited from being withdrawn, or backed out of apertures 134, thereby securely engaging insulator 124 atop jaw frame 122. Although two snap-fit members 132 and apertures 134 are shown, greater or fewer than two snap-fit members 132 and apertures 134 may be provided. Further, any other suitable mechanism for engaging insulator 124 and jaw frame 122 may alternatively be provided. Injection-molding insulator 124 is particularly advantageous in that injection-molding provides a relatively simple and inexpensive process for forming insulator 124 including snap-fit members 132 (or any other suitable engagement structures, e.g., tabs 232 of insulator 224 (FIGS. 6A-6C)).

Figure 6A:
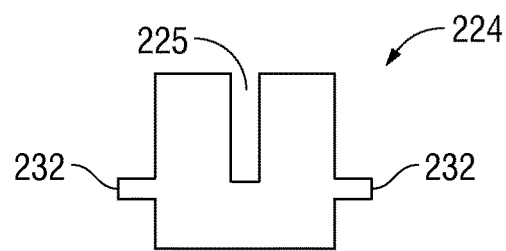
FIG. 6A is a transverse, cross-sectional view of another embodiment of an insulator configured for use with one of the jaw members of the end effector assembly of FIG. 3.
Figure 6B:
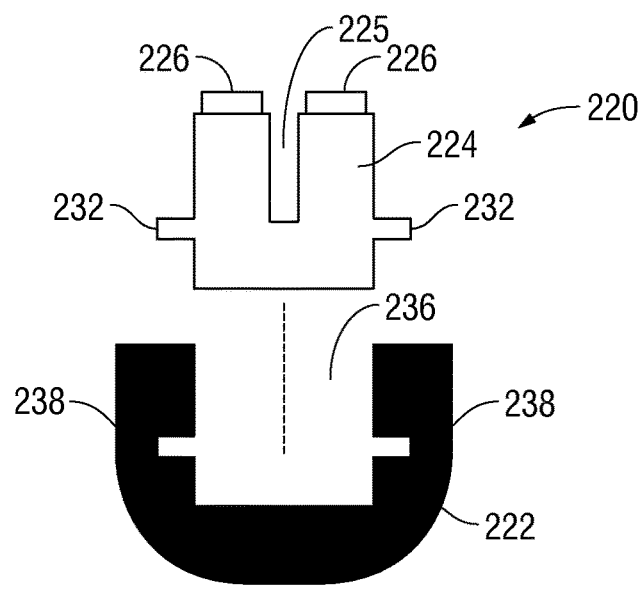
FIG. 6B is a transverse, cross-sectional view of the insulator of FIG. 6A including a sealing plate disposed thereon and in position for assembly with a jaw frame of the jaw member.
Figure 6C:
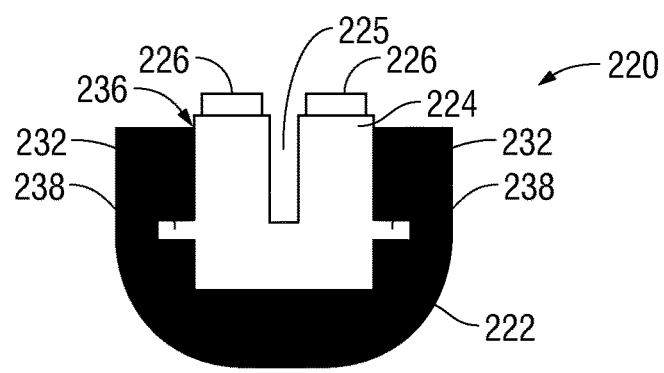
FIG. 6C is a transverse, cross-sectional view of the jaw member of FIG. 6B in an assembled condition.

Turning now to FIGS. 6A-6C, the configuration and manufacture of jaw member 220 in accordance with another embodiment of the present disclosure is described. Insulator 224 is formed from an electrically-insulative material, e.g., via injection molding, and includes a pair of opposed, outwardly-extending tabs 232 extending therefrom. Insulator 224 further includes a knife channel 225 defined therein and extending longitudinally therethrough. Knife channel 225 is configured to permit reciprocation of a knife blade (not shown) therethrough for cutting tissue grasped between jaw member 220 and the opposed jaw member (not shown) thereof. Once insulator 224 has been formed, e.g., via injection-molding, tissue sealing plate 226 may be formed atop insulator 224 via vapor deposition, e.g., physical vapor deposition or chemical vapor deposition, or other suitable deposition process.

Continuing with reference to FIGS. 6A-6C, and to FIG. 6B in particular, with tissue sealing plate 226 formed atop insulator 224, insulator 224 and tissue sealing plate 226 may be engaged within jaw frame 222. As shown in FIG. 6B, jaw frame 222 defines a cavity 236 that is shaped complementary to insulator 224 and is configured to receive insulator 224 at least partially therein. Jaw frame 222 further includes a pair of notches 238 defined within the inner surface thereof formed by cavity 236. Notches 238 are configured to receive tabs 232 of insulator 224 therein to engage jaw frame 222 and insulator 224 to one another, as will be described below.

Referring still to FIGS. 6A-6C and, more particularly, to FIG. 6C, in order to engage insulator 224 and tissue sealing plate 226 to jaw frame 222, insulator 224 is urged into cavity 236 defined within jaw frame 222. More specifically, insulator 224 may defined a diameter substantially similar, or slightly smaller than that of jaw frame 222 to establish a press-fit, or friction-fit engagement therebetween. As such, tabs 232 extending from insulator 224 are resiliently flexed, or compressed to permit advancement of insulator 224 into jaw frame 222. Upon further advancement of insulator 224 into cavity 236 of jaw frame 222, tabs 232 of insulator 224 are positioned adjacent notches 238 defined within jaw frame 222. Once tabs 232 are moved into position adjacent notches 238, tabs 232 are permitted to resiliently return to their initial position such that tabs 232 are biased into engagement with notches 238 to engage insulator 224 and jaw frame 222 to one another. Insulator 224 may include a plurality of tabs 232 extending therefrom in any configuration and/or tabs 232 may define elongated configurations extending along the length of insulator 224. Notches 238 are configured complementarily to tabs 232 and, thus, the number and/or configuration of notches 238 defined within jaw frame 222 may depend at least in part on the number and/or configuration of tabs 232.

Referring now to FIGS. 7A-9, various electrical connections for electrically coupling tissue sealing plate 126 of jaw member 120 to the source of electrosurgical energy (not shown) are described. Although reference is made to jaw member 120, it is envisioned that the electrical connections described herein may alternatively be used in conjunction with any of the other jaw members described herein, or any other suitable jaw member, in particular a jaw member including a jaw frame and an insulator engaged to the jaw frame that has a tissue sealing plate formed thereon via vapor deposition.

Figure 7A:
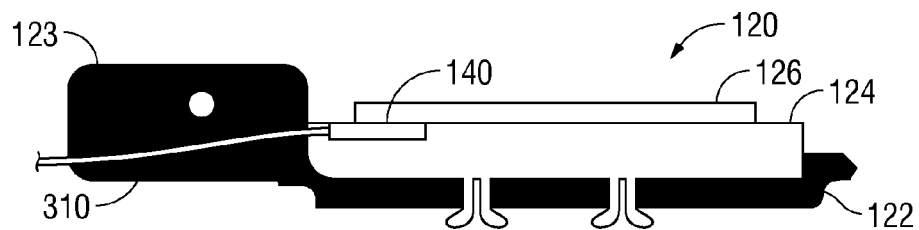
FIG. 7A is a longitudinal, cross-sectional view of the jaw member of FIG. 5C including an electrical connection in accordance with one embodiment of the present disclosure.
Figure 7B:
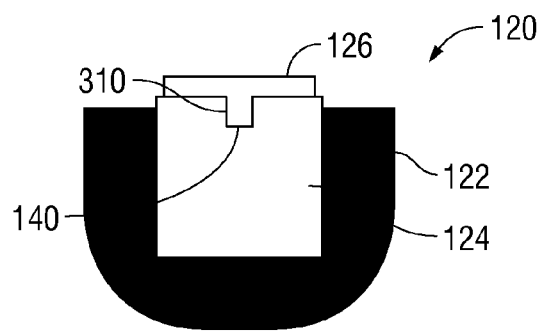
FIG. 7B is a transverse, cross-sectional view of the jaw member of FIG. 7A.

One electrical connection is shown in FIGS. 7A-7B and includes wire 310 for electrically coupling tissue sealing plate 126 of jaw member 120 to a source of energy (not shown) to energizing tissue sealing plate 126 (and/or tissue sealing plate 116 (FIGS. 3-4)) for sealing tissue grasped between tissue sealing plates 116, 126 of respective jaw members 110, 120 (see FIGS. 3-4). More specifically, insulator 124 may include a groove, or slot 140 defined therein, e.g., formed therein during injection molding of insulator 124, that is configured to receive wire 310 therein to permit electrical communication between wire 310 and tissue sealing plate 126. In other words, wire 310 is positioned within slot 140 of insulator 124 prior to the vapor deposition of tissue sealing plate 126 thereon such that, upon deposition of tissue sealing plate 126 atop insulator 124, a portion of tissue sealing plate 126 is deposited atop the portion of wire 310 disposed within slot 140 of insulator 124. As such, with wire 310 contacting tissue sealing plate 126 after formation of tissue sealing plate 126 about insulator 124, electrosurgical energy may be supplied to tissue sealing plate 126 via wire 310 to seal tissue grasped between tissue sealing plates 116, 126 of jaw members 110, 120, respectively (see FIGS. 3-4). Further, wire 310 may be molded, friction-fit, or otherwise engaged within slot 140 of insulator 124 to maintain the engagement of wire 310 within slot 140 and, thus, to maintain the electrical communication between wire 310 and tissue sealing plate 126.

Figure 8A:
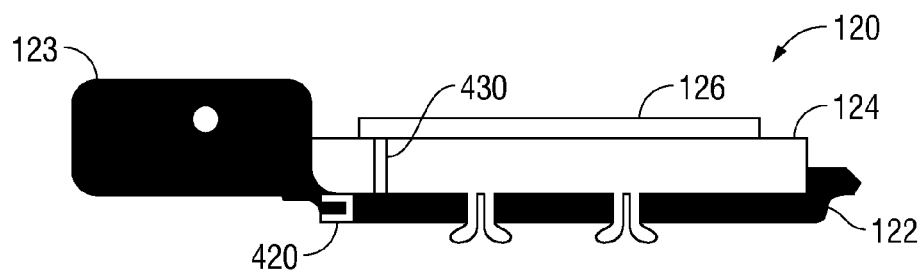
FIG. 8A is a longitudinal, cross-sectional view of the jaw member of FIG. 5C including yet another embodiment of an electrical connection provided in accordance with the present disclosure.
Figure 8B:
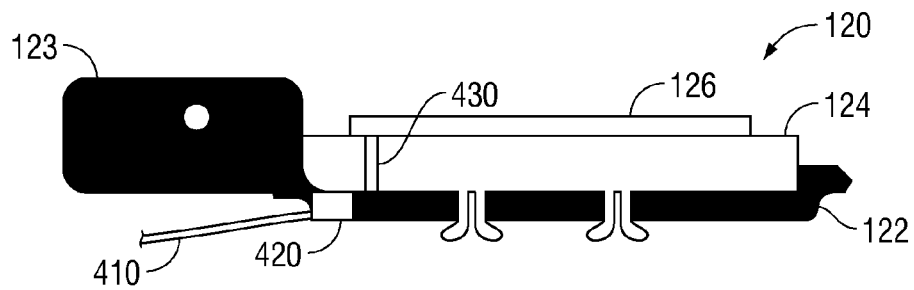
FIG. 8B is a transverse, cross-sectional view of the jaw member of FIG. 8A.

FIGS. 8A-8B show another embodiment of an electrical connection for electrically coupling tissue sealing plate 126 to a source of energy (not shown) via wire 410. The electrical connection includes a plated aperture 420 formed within jaw frame 122 for soldering wire 410 thereto, thus electrically coupling wire 410 to jaw frame 122. Insulator 124 may include a lumen extending therethrough that is configured to receive an electrically conductive post 430 therein for electrically coupling tissue sealing plate 126 to jaw frame 122, although any other suitable configuration for electrically coupling tissue sealing plate 126 and jaw frame 122 may alternatively be provided. Thus, with wire 410 electrically coupled to jaw frame 122 and with jaw frame 122 electrically coupled to tissue sealing plate 126, electrosurgical energy may be supplied to tissue sealing plate 126 via wire 410, jaw frame 122, and post 430, to seal tissue grasped between tissue sealing plates 116, 126 of jaw members 110, 120, respectively (see FIGS. 3-4).

Figure 9:
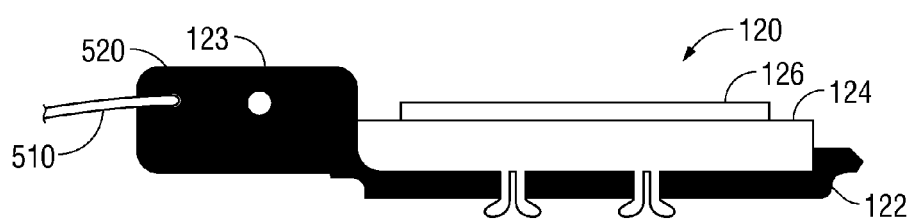
FIG. 9 is a longitudinal, cross-sectional view of the jaw member of FIG. 5C including another embodiment of an electrical connection provided in accordance with the present disclosure.

FIG. 9 shows another electrical connection similar to the previous electrical connection except that plated aperture 520 is formed within proximal flange 123. Wire 510 is soldered to proximal flange 123 via plated aperture 520, electrically coupling wire 510 to jaw frame 122. Jaw frame 122 is electrically coupled to tissue sealing plate 126 via any suitable electrical connection such that energy may be supplied via wire 510 to tissue sealing plate 126 for sealing tissue grasped between tissue sealing plates 116, 126 of jaw members 110, 120, respectively (see FIGS. 3-4).

From the foregoing and with reference to the various figure drawings, those skilled in the art will appreciate that certain modifications can also be made to the present disclosure without departing from the scope of the same. While several embodiments of the disclosure have been shown in the drawings, it is not intended that the disclosure be limited thereto, as it is intended that the disclosure be as broad in scope as the art will allow and that the specification be read likewise. Therefore, the above description should not be construed as limiting, but merely as exemplifications of particular embodiments. Those skilled in the art will envision other modifications within the scope and spirit of the claims appended hereto.

What is claimed is:

1. A method of manufacturing a jaw member of a surgical instrument, comprising:
   forming a substrate via injection molding;
   forming an electrically-conductive member on a surface of the substrate via vapor deposition; and
   engaging the substrate to a jaw frame, the jaw frame defining a cavity for receiving the substrate.

2. The method according to claim 1, wherein the vapor deposition includes physical vapor deposition.

3. The method according to claim 1, wherein the vapor deposition includes chemical vapor deposition.

4. The method according to claim 1, further comprising molding a wire to the substrate prior to forming the electrically-conductive member on the surface of the substrate.

5. The method according to claim 4, wherein the electrically-conductive member is formed on the surface of the substrate such that the electrically-conductive member is in electrical communication with the wire.

6. The method according to claim 1, wherein engaging the substrate to the jaw frame includes snap-fitting the substrate to the jaw frame.

7. A method of manufacturing a surgical instrument, comprising:
   forming a first substrate of a first jaw member via injection molding of an electrically insulative material;
   depositing a first electrically-conductive member on a first surface of the first substrate via vapor deposition;
   engaging the first substrate within a cavity defined by a jaw frame of the first jaw member to secure the first substrate to the first jaw member;
   depositing a second electrically-conductive member on a second surface of a second jaw member via vapor deposition; and
   coupling the first jaw member to the second jaw member to permit movement of at least one of the first and second jaw members relative to the other between a spaced-apart position and an approximated position for grasping tissue between the jaw members, the first surface opposing the second surface.

8. The method according to claim 7, wherein the vapor deposition includes physical vapor deposition.

9. The method according to claim 7, wherein the vapor deposition includes chemical vapor deposition.

10. The method according to claim 7, wherein engaging the first substrate within the cavity of the jaw frame of the first jaw member includes snap-fitting the substrate within the jaw frame.

11. The method according to claim 7, wherein engaging the first substrate within the cavity of the jaw frame of the first jaw member includes friction-fitting the substrate within the jaw frame.

12. The method according to claim 7, further comprising pivotably coupling a proximal flange of the first jaw member to a proximal flange of the second jaw member to permit movement of at least one of the jaw members relative to the other between the spaced-apart position and the approximated position.

13. The method according to claim 7, further comprising molding a wire within the first jaw member such that the wire is disposed in electrical communication with the first electrically-conductive member for supplying energy to the first electrically-conductive member.

14. A method of manufacturing a jaw member of a surgical instrument, comprising:
   injection molding a substrate of electrically insulative material; and
   vapor depositing an electrically-conductive member on a surface of the substrate.

15. The method according to claim 14, further comprising coupling a wire to the substrate prior to vapor depositing the electrically-conductive member thereon such that, upon depositing the electrically-conductive member on the surface of the substrate, the wire is electrically coupled to the electrically-conductive member for providing energy to the electrically-conductive member.

* * * * *